(12) United States Patent
Reevell

(10) Patent No.: US 11,337,459 B2
(45) Date of Patent: May 24, 2022

(54) AEROSOL-GENERATING ARTICLE HAVING MULTIPLE FUSES

(71) Applicant: Philip Morris Products S.A., Neuchatel (CH)

(72) Inventor: Tony Reevell, London (GB)

(73) Assignee: Philip Morris Products S.A., Neuchatel (CH)

( * ) Notice: Subject to any disclaimer, the term of this patent is extended or adjusted under 35 U.S.C. 154(b) by 513 days.

(21) Appl. No.: 16/080,266

(22) PCT Filed: Mar. 8, 2017

(86) PCT No.: PCT/EP2017/055431
§ 371 (c)(1),
(2) Date: Aug. 27, 2018

(87) PCT Pub. No.: WO2017/153467
PCT Pub. Date: Sep. 14, 2017

(65) Prior Publication Data
US 2019/0045844 A1 Feb. 14, 2019

(30) Foreign Application Priority Data
Mar. 9, 2016 (EP) .................................... 16159517

(51) Int. Cl.
*A24F 13/00* (2006.01)
*A24F 40/46* (2020.01)
(Continued)

(52) U.S. Cl.
CPC ............... *A24F 40/46* (2020.01); *A24D 1/20* (2020.01); *A24F 40/50* (2020.01); *A61M 15/06* (2013.01);
(Continued)

(58) Field of Classification Search
CPC ....................................................... A24F 47/00
(Continued)

(56) References Cited

U.S. PATENT DOCUMENTS

| 5,505,214 A | 4/1996 | Collins et al. |
| 5,613,504 A | 3/1997 | Collins et al. |

(Continued)

FOREIGN PATENT DOCUMENTS

| CN | 103338663 A | 10/2013 |
| CN | 104010529 A | 8/2014 |

(Continued)

OTHER PUBLICATIONS

International Search Report and Written Opinion dated Jun. 7, 2017 in PCT/EP2017/055431 filed Mar. 8, 2017.
(Continued)

*Primary Examiner* — Phuong K Dinh
(74) *Attorney, Agent, or Firm* — Oblon, McClelland, Maier & Neustadt, L.L.P.

(57) ABSTRACT

There is provided an aerosol-generating article including an aerosol-forming substrate and a plurality of electrical fuses. The plurality of electrical fuses are spaced apart from each other, each electrical fuse disposed proximate a portion of the aerosol-forming substrate. There is also provided an aerosol-generating device for the aerosol-generating article, an aerosol-generating system including the aerosol-generating article and the aerosol-generating device, and a controller for the aerosol-generating device.

14 Claims, 4 Drawing Sheets

(51) Int. Cl.
*A24D 1/20* (2020.01)
*A24F 40/50* (2020.01)
*A61M 15/06* (2006.01)
*H05B 1/02* (2006.01)
*A24F 40/20* (2020.01)
*H05B 3/40* (2006.01)

(52) U.S. Cl.
CPC ............ H05B 1/0244 (2013.01); *A24F 40/20* (2020.01); *A61M 2205/8206* (2013.01); *H05B 3/40* (2013.01)

(58) Field of Classification Search
USPC .................................................. 131/328–329
See application file for complete search history.

(56) References Cited

U.S. PATENT DOCUMENTS

| | | | |
|---|---|---|---|
| 5,692,291 | A | 12/1997 | Deevi et al. |
| 5,730,158 | A | 3/1998 | Collins et al. |
| 5,865,185 | A | 2/1999 | Collins et al. |
| 7,073,731 | B2 | 7/2006 | Hess et al. |
| 2006/0107965 | A1 | 5/2006 | Marshall |
| 2011/0126848 | A1 | 6/2011 | Zuber et al. |
| 2013/0319435 | A1* | 12/2013 | Flick .............. A61M 11/042 131/328 |
| 2014/0253144 | A1 | 9/2014 | Novak, III et al. |
| 2015/0075545 | A1 | 3/2015 | Xiang |
| 2015/0181934 | A1 | 7/2015 | Lyubomirskiy et al. |
| 2015/0181936 | A1 | 7/2015 | Lyubomirskiy et al. |
| 2015/0230521 | A1 | 8/2015 | Talon |
| 2015/0272226 | A1 | 10/2015 | Zuber et al. |
| 2016/0174613 | A1 | 6/2016 | Zuber et al. |

FOREIGN PATENT DOCUMENTS

| | | |
|---|---|---|
| CN | 104812260 A | 7/2015 |
| CN | 105163610 A | 12/2015 |
| EP | 0 503 767 A1 | 9/1992 |
| EP | 0 917 831 A1 | 5/1999 |
| EP | 2 327 318 A1 | 6/2011 |
| EP | 2 468 118 A1 | 6/2012 |
| EP | 1 489 931 B1 | 8/2013 |
| EP | 2 797 448 | 11/2014 |
| JP | 5-115272 A | 5/1993 |
| RU | 2 517 125 C2 | 5/2014 |
| WO | WO 2013/098397 A2 | 7/2013 |

OTHER PUBLICATIONS

Russian Federation Office Action dated Sep. 23, 2020 in Patent Application No. 2018130656/03(049854) (with English translation), citing document AO therein, 15 pages.

Combined Chinese Office Action and Search Report dated Nov. 11, 2020 in corresponding Chinese Patent Application No. 201780011671.X (with English Translation) citing documents AA-AC, AO-AR therein, 10 pages.

Extended European Search Report dated Sep. 8, 2016 in Patent Application No. 16159517.8.

Office Action dated Feb. 15, 2021 in corresponding Japanese Patent Application No. 2018-546816 (with English Translation), citing document AO therein, 5 pages.

* cited by examiner

AEROSOL-GENERATING ARTICLE HAVING MULTIPLE FUSES

TECHNICAL FIELD

The present invention relates to an aerosol-generating article having multiple fuses, an aerosol-generating device suitable for use with the aerosol-generating article, and an aerosol-generating system comprising the aerosol-generating article and the aerosol-generating device. The invention finds particular application as an electrically operated smoking system.

DESCRIPTION OF THE RELATED ART

One type of aerosol-generating system is an electrically operated smoking system. Known handheld electrically operated smoking systems typically comprise an aerosol-generating device comprising a battery, control electronics and an electric heater for heating an aerosol-generating article designed specifically for use with the aerosol-generating device. In some examples, the aerosol-generating article comprises an aerosol-forming substrate, such as a tobacco rod or a tobacco plug, and the heater contained within the aerosol-generating device is inserted into or around the aerosol-forming substrate when the aerosol-generating article is inserted into the aerosol-generating device.

In some cases, the electric heater may comprise multiple heating elements configured to heat different portions of the aerosol-forming substrate. It may be desirable to heat the different portions of the aerosol-forming substrate sequentially. However, in such cases it is typically necessary to retain the aerosol-generating article within the aerosol-generating device until all portions of the aerosol-forming substrate have been heated. Removing the article when only some of the portions of the aerosol-forming substrate have been heated and subsequently reinserting the article into the device may result in re-heating of portions of the substrate that have been heated previously. This may result in a diminished smoking experience for a user of the smoking system.

It would be desirable to provide an aerosol-generating article that facilitates sequential heating of portions of an aerosol-forming substrate.

SUMMARY

According to a first aspect of the present invention there is provided an aerosol-generating article comprising an aerosol-forming substrate and a plurality of electrical fuses. The plurality of electrical fuses are spaced apart from each other, each electrical fuse positioned proximate a portion of the aerosol-forming substrate.

BRIEF DESCRIPTION OF THE DRAWINGS

Embodiments of the invention will now be described, by way of example only, with reference to the accompanying drawings, in which.

DETAILED DESCRIPTION

Figure 1:
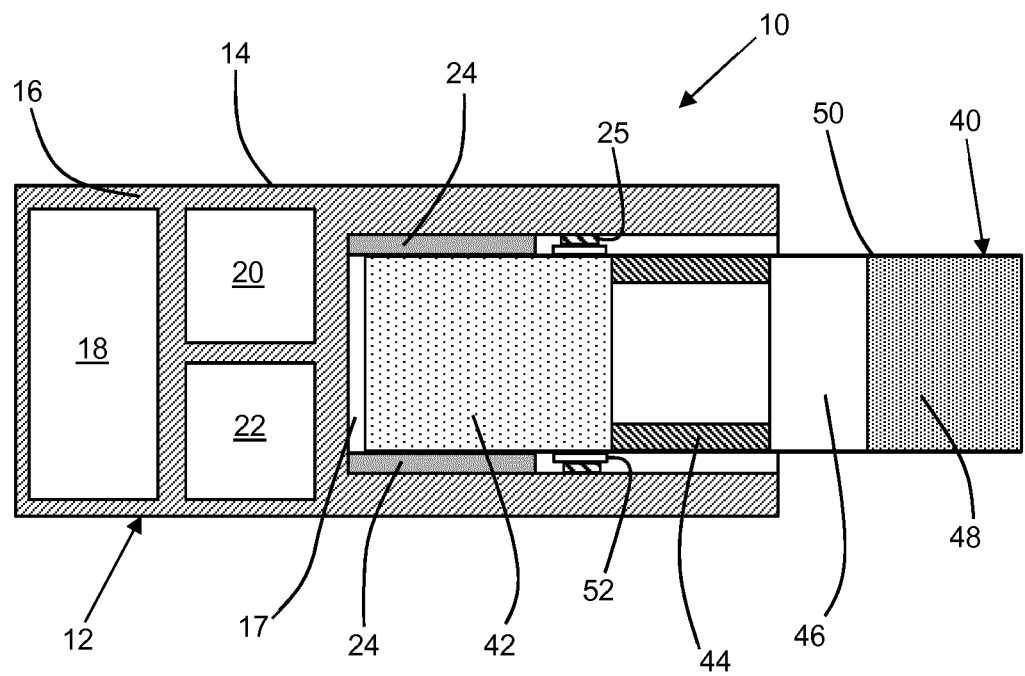
FIG. 1 shows an aerosol-generating system according to an embodiment of the present invention.

As used herein, the term "aerosol-generating article" refers to an article comprising an aerosol-forming substrate that, when heated in an aerosol-generating device, releases volatile compounds that can form an aerosol. An aerosol-generating article is separate from and configured for combination with an aerosol-generating device for heating the aerosol-generating article.

As used herein, the term "electrical fuse" refers to an electrical switch that functions as an electrical conductor when in a closed state, and wherein the electrical fuse may be irreversibly switched into an open state in which the electrical fuse no longer functions as an electrical conductor.

Aerosol-generating articles according to the present invention comprise a plurality of spaced apart electrical fuses, each electrical fuse positioned proximate a portion of an aerosol-forming substrate. Advantageously, such an arrangement of electrical fuses can facilitate sequential heating of the different portions of the aerosol-forming substrate. In particular, the aerosol-generating article can be combined with a device configured to sequentially heat the portions of the aerosol-forming substrate, wherein each electrical fuse may function as a record of whether the associated portion of the aerosol-forming substrate has been heated. That is, each electrical fuse may be opened to record when the associated portion of the aerosol-forming substrate has been heated. Therefore, advantageously, providing the fuses as part of the aerosol-generating article to record which portions of the aerosol-forming substrate have been heated may prevent reheating of those portions of the aerosol-forming substrate.

Furthermore, since the electrical fuses form part of the aerosol-generating article, the record of which portions of the aerosol-forming substrate have been heated is retained even when the article is removed from the device. Therefore, aerosol-generating articles according to the present invention facilitate partial heating of the aerosol-forming substrate, removal of the aerosol-generating article from the device, and subsequent recombination of the article with the device for heating of the remaining portions of the aerosol-forming substrate. Advantageously, this may facilitate a user only partially heating the aerosol-forming substrate, removing the article from the device for safe storage, and then subsequently recombining the article with the device for heating the remainder of the aerosol-forming substrate.

Advantageously, providing the fuses as part of the aerosol-generating article to record which portions of the aerosol-forming substrate have been heated may eliminate the need to recombine the aerosol-generating article with the aerosol-generating device in a particular orientation. That is, the aerosol-generating device may be configured to determine which portions of the aerosol-forming substrate have already been heated based on the state of each electrical fuse, regardless of the orientation of the aerosol-generating article with respect to the aerosol-generating device.

Each of the plurality of electrical fuses may be positioned within a portion of the aerosol-forming substrate. Each of the plurality of electrical fuses may be positioned about an exterior portion of the aerosol-forming substrate. Some of the electrical fuses may be positioned within a portion of the aerosol-forming substrate and some of the electrical fuses may be positioned about an exterior portion of the aerosol-forming substrate.

Preferably, each electrical fuse is configured to open when a potential difference across the electrical fuse exceeds about 3 volts. Typical aerosol-generating devices comprise a power supply configured to operate at a voltage of between about 3 volts and about 6 volts. Therefore, configuring each fuse to open at a potential difference of at least about 3 volts facilitates the use of aerosol-generating articles according to the present invention with aerosol-generating devices using conventional power supplies.

Suitable materials for forming each electrical fuse include aluminium, copper, zinc, silver, and alloys thereof.

Preferably, the aerosol-generating article comprises at least three article electrical contacts, wherein each electrical fuse extends between and is electrically connected to a pair of the article electrical contacts. Advantageously, providing article electrical contacts so that each electrical fuse extends between a pair of article electrical contacts may facilitate electrical connection of each end of each electrical fuse to an electrical circuit of an aerosol-generating device. For example, an aerosol-generating device may be configured to measure the electrical resistance between each pair of article electrical contacts to determine whether the electrical fuse extending between the pair of article electrical contacts is closed or open.

To facilitate electrical connection of each article electrical contact to an electrical contact on an aerosol-generating device, preferably each article electrical contact has a larger surface area than the surface area of each electrical fuse connected to the article electrical contact. Preferably, each article electrical contact has a surface area at least two times larger than the surface area of each electrical fuse connected to the article electrical contact.

To prevent damage to each article electrical contact when an electrical fuse connected to the article electrical contact is opened, preferably each article electrical contact has a lower electrical resistance than the electrical resistance of each electrical fuse connected to the article electrical contact.

Each article electrical contact may have a larger cross-sectional area than the cross-sectional area of each electrical fuse connected to the article electrical contact. For each electrical fuse, cross-sectional area is measured perpendicular to the direction extending along the electrical fuse between the pair of article electrical contacts to which the electrical fuse is connected. For each article electrical contact, cross-sectional area corresponds to the surface area of a face of the article electrical contact configured to contact an electrical contact on an aerosol-generating device.

Each article electrical contact may be formed from a material having a lower resistivity than a material from which each electrical fuse connected to the article electrical contact is formed.

Suitable materials for forming the article electrical contacts include aluminium, copper, zinc, silver, and alloys thereof.

Preferably, each article electrical contact is integrally formed with each electrical fuse connected to the article electrical contact. That is, each article electrical contact and each electrical fuse connected to the article electrical contact are preferably formed from a single piece of electrically conductive material.

The aerosol-forming substrate may comprise a substantially cylindrical outer surface, wherein the article electrical contacts and the electrical fuses each extend over a portion of the cylindrical outer surface.

Each article electrical contact may be connected to only a single electrical fuse.

The article electrical contacts and the electrical fuses may be connected in series so that each article electrical contact is electrically connected to at least two electrical fuses and so that the article electrical contacts and the electrical fuses form a continuous ring around a portion of the cylindrical outer surface of the aerosol-forming substrate. Such an arrangement may facilitate the combination of the aerosol-generating article with an aerosol-generating device using any rotational orientation. For example, an aerosol-generating device may comprise a tubular cavity for receiving the aerosol-generating article and a ring of device electrical contacts configured to electrically connect to the article electrical contacts in any rotational orientation.

Each article electrical contact may have a substantially annular shape, wherein the article electrical contacts are spaced apart along at least a portion of the cylindrical outer surface of the aerosol-forming substrate. In such embodiments, the article electrical contacts may be spaced apart in a length direction along at least a portion of the cylindrical outer surface of the aerosol-forming substrate, wherein each electrical fuse extends substantially in the length direction between consecutive article electrical contacts.

The at least three article electrical contacts may comprise a common article electrical contact and a plurality of sensing article electrical contacts, wherein each electrical fuse extends between a sensing article electrical contact and the common article electrical contact. Providing a common article electrical contact connected to all of the electrical fuses may advantageously minimise the number of article electrical contacts.

The aerosol-forming substrate may comprise a substantially cylindrical outer surface, wherein the common article electrical contact has a substantially annular shape and extends around a portion of the substantially cylindrical outer surface. Providing a substantially annular common article electrical contact may facilitate connection of the common article electrical contact to a corresponding device electrical contact on an aerosol-generating device, regardless of the rotational orientation of the aerosol-generating article with respect to the aerosol-generating device.

The aerosol-forming substrate may be substantially elongate and comprise an end face, wherein the article electrical contacts are positioned on the end face of the aerosol-forming substrate. In those embodiments in which the aerosol-generating article comprises a common article electrical contact, the common article electrical contact is preferably positioned at the centre of the end face. Providing a common article electrical contact at the centre of the end face may facilitate connection of the common article electrical contact to a corresponding device electrical contact on an aerosol-generating device, regardless of the rotational orientation of the aerosol-generating article with respect to the aerosol-generating device. Preferably, the sensing article electrical contacts are spaced around the common article electrical contact.

The aerosol-forming substrate may comprise a solid aerosol-forming substrate. The aerosol-forming substrate may comprise tobacco. The aerosol-forming substrate may comprise a tobacco-containing material containing volatile tobacco flavour compounds which are released from the substrate upon heating. The aerosol-forming substrate may comprise a non-tobacco material. The aerosol-forming substrate may comprise tobacco-containing material and non-tobacco containing material.

The aerosol-forming substrate may include at least one aerosol-former. Suitable aerosol-formers include, but are not limited to: polyhydric alcohols, such as propylene glycol, triethylene glycol, 1,3-butanediol and glycerine; esters of polyhydric alcohols, such as glycerol mono-, di- or triacetate; and aliphatic esters of mono-, di- or polycarboxylic acids, such as dimethyl dodecanedioate and dimethyl tetradecanedioate.

Preferred aerosol formers are polyhydric alcohols or mixtures thereof, such as propylene glycol, triethylene glycol, 1,3-butanediol and, most preferred, glycerine.

The aerosol-forming substrate may comprise a single aerosol former. Alternatively, the aerosol-forming substrate may comprise a combination of two or more aerosol formers.

The aerosol-forming substrate may have an aerosol former content of greater than 5 percent on a dry weight basis.

The aerosol-forming substrate may have an aerosol former content of between approximately 5 percent and approximately 30 percent on a dry weight basis.

The aerosol-forming substrate may have an aerosol former content of approximately 20 percent on a dry weight basis.

In those embodiments in which the aerosol-forming substrate comprises a solid aerosol-forming substrate, the solid aerosol-forming substrate may comprise a unitary aerosol-forming substrate, wherein each electrical fuse is positioned proximate a portion of the unitary aerosol-forming substrate. The unitary aerosol-forming substrate may comprise a single rod, plug or sheet of solid aerosol-forming material, wherein each electrical fuse is positioned proximate a portion of the rod, plug or sheet of solid aerosol-forming material.

In those embodiments in which the aerosol-forming substrate comprises a solid aerosol-forming substrate, the solid aerosol-forming substrate may comprise a plurality of discrete portions of solid aerosol-forming material, wherein each electrical fuse is positioned proximate one of the discrete portions of solid aerosol-forming material. The plurality of discrete portions of solid aerosol-forming material may be spaced apart from each other and provided on a base layer. The base layer may comprise a sheet on which the plurality of discrete portions of solid aerosol-forming material are provided.

The aerosol-forming substrate may comprise a liquid aerosol-forming substrate. The liquid aerosol-forming substrate may comprise a nicotine solution. The liquid aerosol-forming substrate preferably comprises a tobacco-containing material comprising volatile tobacco flavour compounds which are released from the liquid upon heating. The liquid aerosol-forming substrate may comprise a non-tobacco material. The liquid aerosol-forming substrate may include water, solvents, ethanol, plant extracts and natural or artificial flavours. Preferably, the liquid aerosol-forming substrate further comprises an aerosol former.

Preferably, the liquid aerosol-forming substrate comprises a liquid aerosol-forming material impregnated into a plurality of discrete portions of carrier material, where each discrete portion of carrier material impregnated with the liquid aerosol-forming material forms a portion of the aerosol-forming substrate. Each electrical fuse is positioned proximate one of the discrete portions of carrier material.

Preferably, the carrier material has a density of between about 0.1 grams/cubic centimetre and about 0.3 grams/cubic centimetre.

Preferably, the carrier material has a porosity of between about 15 percent and about 55 percent.

The carrier material may comprise one or more of glass, cellulose, ceramic, stainless steel, aluminium, polyethylene (PE), polypropylene, polyethylene terephthalate (PET), poly (cyclohexanedimethylene terephthalate) (PCT), polybutylene terephthalate (PBT), polytetrafluoroethylene (PTFE), expanded polytetrafluoroethylene (ePTFE), and BAREX®.

Preferably, the carrier material is chemically inert with respect to the liquid aerosol-forming material.

Each discrete portion of carrier material may have any suitable shape and size. For example, each discrete portion of carrier material may be in the form of a sheet or a plug.

The present invention also extends to aerosol-generating devices suitable for use with aerosol-generating articles according to the first aspect of the present invention. Therefore, according to a second aspect of the present invention there is provided an aerosol-generating device comprising a housing defining a cavity for receiving an aerosol-generating article, a supply of electrical energy, and a plurality of electrical heaters positioned within the cavity. The aerosol-generating device further comprises at least three device electrical contacts positioned within the cavity and configured to electrically connect to a plurality of electrical fuses on an aerosol-generating article when an aerosol-generating article is received within the cavity. Each electrical heater is associated with a pair of the device electrical contacts. The aerosol-generating device also comprises a controller configured to measure electrical resistance between each pair of the device electrical contacts when an aerosol-generating article is received within the cavity. The controller is further configured to control a supply of electrical energy to each of the electrical heaters based on the measured electrical resistance between the corresponding pair of device electrical contacts. Preferably, the controller is configured to measure the electrical resistance between each pair of device electrical contacts and control the supply of electrical energy to the corresponding electrical heater sequentially. That is, preferably the controller is configured to measure the electrical resistance for one pair of device electrical contacts and control the supply of energy for a single electrical heater before repeating the process for the next pair of device electrical contacts and the corresponding electrical heater.

By measuring the electrical resistance between each pair of device electrical contacts, aerosol-generating devices according to the present invention can advantageously determine whether an electrical fuse extending between and connected to a pair of article electrical contacts in electrical contact with the pair of device electrical contacts is closed or open. That is, a closed electrical fuse exhibits a relatively low electrical resistance and an open electrical fuse exhibits a relatively high electrical resistance.

In the event that the controller determines that a particular electrical fuse of an aerosol-generating article received within the cavity is closed, the controller is configured to control a supply of electrical energy to one of the electrical heaters positioned proximate the closed electrical fuse to heat a portion of an aerosol-generating substrate positioned proximate the electrical heater and the closed fuse.

Preferably, at a predetermined time after activating the electrical heater, the controller is configured to cease the supply of electrical energy to the electrical heater. Preferably, the controller is configured to activate a supply of electrical energy to the closed fuse, via the corresponding pair of device electrical contacts and a corresponding pair of article electrical contacts, to open the closed fuse. The controller may be configured to open the closed fuse before activating the electrical heater. The controller may be configured to open the closed fuse while the electrical heater is active. The controller may be configured to open the closed fuse after ceasing the supply of electrical energy to the electrical heater.

In the event that the controller determines that a particular electrical fuse of an aerosol-generating article received within the cavity is open, the controller is preferably configured to inhibit the supply of electrical energy to the electrical heater positioned proximate the open fuse while the aerosol-generating article remains in the cavity. Therefore, advantageously, the aerosol-generating device can be configured to prevent heating of a portion of an aerosol-forming substrate, proximate an open fuse, which has already been heated.

The at least three device electrical contacts may comprise a common device electrical contact and a plurality of sensing device electrical contacts, wherein the controller is configured to measure electrical resistance between each of the sensing device electrical contacts and the common device electrical contact when an aerosol-generating device is received within the cavity. Providing a common device electrical contact may advantageously minimise the number of device electrical contacts.

The cavity may comprise a substantially cylindrical inner surface, wherein the common device electrical contact has a substantially annular shape and extends around a portion of the substantially cylindrical inner surface. Providing a substantially annular common device electrical contact may facilitate connection of the common device electrical contact to a corresponding article electrical contact on an aerosol-generating article, regardless of the rotational orientation of the aerosol-generating article with respect to the aerosol-generating device.

The cavity may comprise an end face, wherein the device electrical contacts are positioned on the end face of the cavity. In those embodiments in which the aerosol-generating device comprises a common device electrical contact, the common device electrical contact is preferably positioned at the centre of the end face. Providing a common device electrical contact at the centre of the end face may facilitate connection of the common device electrical contact to a corresponding article electrical contact on an aerosol-generating article, regardless of the rotational orientation of the aerosol-generating article with respect to the aerosol-generating device. Preferably, the sensing device electrical contacts are spaced around the common device electrical contact.

The aerosol-generating device may be configured so that electrical energy can be supplied to each electrical heater only via a closed electrical fuse on an aerosol-generating article when the aerosol-generating article is received within the cavity. That is, the aerosol-generating device may be configured so that, when an aerosol-generating article is received within the cavity, each electrical fuse forms part of an electrical circuit between the supply of electrical energy and an electrical heater. Such an arrangement may advantageously prevent reheating of a portion of an aerosol-forming substrate that has already been heated, since an open fuse provides galvanic isolation of the corresponding electrical heater from the supply of electrical energy.

At least some of the device electrical contacts may form part of a corresponding electrical heater. Alternatively, the device electrical contacts may be provided separately from the electrical heaters.

Each of the electrical heaters may be an inductive heater. Preferably, each of the electrical heaters is a resistive heater.

The supply of electrical energy may comprise a direct current (DC) source. In preferred embodiments, the supply of electrical energy comprises a battery. The supply of electrical energy may comprise a Nickel-metal hydride battery, a Nickel cadmium battery, or a Lithium based battery, for example a Lithium-Cobalt, a Lithium-Iron-Phosphate or a Lithium-Polymer battery.

According to a third aspect of the present invention there is provided an aerosol-generating system comprising an aerosol-generating article according to the first aspect of the present invention, in accordance with any of the embodiments described herein, in combination with an aerosol-generating device according to the second aspect of the present invention, in accordance with any of the embodiments described above.

Preferably, the device electrical contacts are configured so that each pair of device electrical contacts electrically connects to an electrical fuse regardless of the rotational orientation of the aerosol-generating article within the cavity.

According to a fourth aspect of the present invention, there is provided an aerosol-generating system comprising an aerosol-generating article and an aerosol-generating device. The aerosol-generating article comprises an aerosol-forming substrate and a plurality of electrical fuses spaced apart from each other, each electrical fuse positioned proximate a portion of the aerosol-forming substrate. The aerosol-generating device comprises a housing defining a cavity for receiving the aerosol-generating article, a supply of electrical energy, and a plurality of electrical heaters positioned within the cavity. The aerosol-generating device further comprises at least three device electrical contacts positioned within the cavity, wherein each electrical heater is associated with a pair of the device electrical contacts and wherein each pair of the device electrical contacts is configured to electrically connect to an electrical fuse when the aerosol-generating article is received within the cavity. The aerosol-generating device further comprises a controller configured to perform a number of steps for each electrical heater when an aerosol-generating article is received within the cavity. Firstly, the controller is configured to measure an electrical resistance between the corresponding pair of device electrical contacts. When the measured electrical resistance is indicative of a closed electrical fuse on the aerosol-generating article, the controller is configured to control a first supply of electrical energy to the electrical heater to heat the portion of the aerosol-forming substrate proximate the closed electrical fuse. That is, the first supply of electrical energy is sufficient to heat the portion of the aerosol-forming substrate proximate the closed fuse. The controller is also configured to control a second supply of electrical energy to the corresponding pair of device electrical contacts to open the closed electrical fuse. That is, the second supply of electrical energy is sufficient to open the closed electrical fuse. Preferably, the controller is configured to repeat these steps sequentially for the plurality of electrical heaters. That is, preferably the controller is configured to perform all of the steps for a single electrical heater before repeating the process for the next electrical heater.

The controller may be configured to open a closed fuse before controlling the first supply of electrical energy to the corresponding electrical heater. The controller may be configured to open a closed fuse while simultaneously controlling the first supply of electrical energy to the corresponding electrical heater. The controller may be configured to open a closed fuse after ceasing the first supply of electrical energy to the corresponding electrical heater.

Preferably, the controller is further configured to inhibit the first supply of electrical energy to each electrical heater when the measured electrical resistance is indicative of an open fuse and until the aerosol-generating article is removed from the cavity.

The aerosol-generating system according to the fourth aspect of the present invention may be combined with any of the optional and preferred features described herein with respect to the first, second and third aspects of the present invention.

According to a fifth aspect of the present invention there is provided a controller for an aerosol-generating device, the aerosol-generating device having a power supply and a plurality of electrical heaters. The controller is configured to perform a series of steps when an aerosol-generating article having an aerosol-forming substrate and a plurality of electrical fuses is received within the aerosol-generating device. Firstly, the controller is configured to measure an electrical resistance of one or more of the plurality of electrical fuses on the aerosol-generating article. Then, the controller is configured to select an electrical heater associated with a closed electrical fuse based on the measured electrical resistance. The controller is configured to trigger a first supply of electrical energy from the power supply to the selected electrical heater, the first supply of electrical energy being suitable for heating a portion of the aerosol-forming substrate. The controller is configured to trigger a second supply of electrical energy from the power supply to the closed electrical fuse, the second supply of electrical energy being suitable to open the closed electrical fuse.

The controller may be configured to open a closed fuse before controlling the first supply of electrical energy to the associated electrical heater. The controller may be configured to open a closed fuse while simultaneously controlling the first supply of electrical energy to the associated electrical heater. The controller may be configured to open a closed fuse after ceasing the first supply of electrical energy to the associated electrical heater.

FIG. 1 shows an aerosol-generating system 10 in accordance with an embodiment of the present invention. The aerosol-generating system 10 comprises an aerosol-generating device 12 comprising a housing 14 defining an internal compartment 16 and a cavity 17, the cavity 17 configured to receive an aerosol-generating article.

The aerosol-generating device 12 comprises a supply of electrical energy 18, a feedback device 20, and a controller 22, all positioned within the internal compartment 16. The supply of electrical energy 18 comprises a rechargeable battery. The aerosol-generating device 12 further comprises a plurality of electrical heaters 24 spaced apart from each other and positioned on an internal cylindrical surface of the cavity 17. The aerosol-generating device 12 also comprises a plurality of device electrical contacts 25 spaced apart from each other and positioned on the internal cylindrical surface of the cavity 17. Each electrical heater 24 is associated with a pair of the device electrical contacts 25.

The aerosol-generating system 10 further comprises an aerosol-generating article 40 that is received within a cavity 17 of the aerosol-generating device 12 during use. The aerosol-generating article 40 comprises an aerosol-forming substrate 42, a hollow acetate tube 44, a polymeric filter 46, a mouthpiece 48 and an outer wrapper 50. The aerosol-forming substrate 42 comprises a plug of tobacco and the mouthpiece 48 comprises a plug of cellulose acetate fibres.

Figure 2:
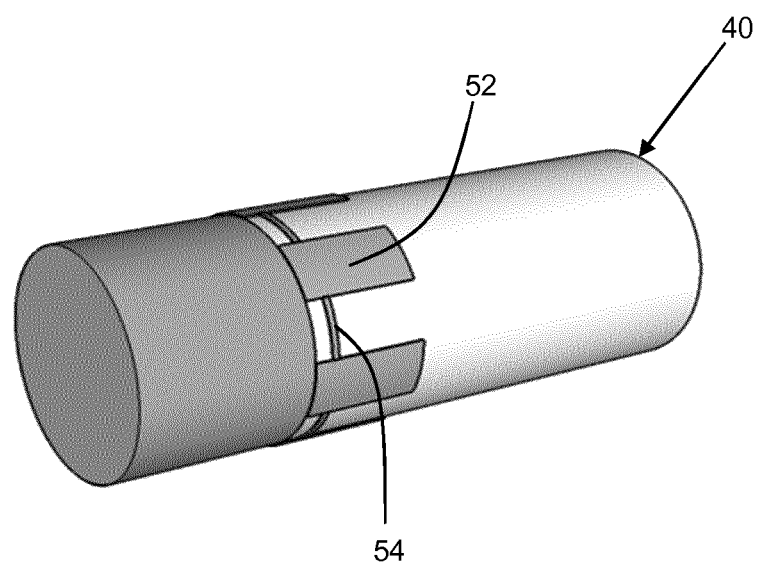
FIG. 2 shows the aerosol-generating article of FIG. 1 and according to a first embodiment of the present invention.

As shown more clearly in FIG. 2, which shows a perspective view of the aerosol-generating article 40, the aerosol-generating article 40 further comprises a plurality of article electrical contacts 52 spaced apart from each other and positioned about a cylindrical outer surface of the aerosol-forming substrate 42. The aerosol-generating article 40 also comprises a plurality of electrical fuses 54, each electrical fuse 54 extending between and electrically connected to a consecutive pair of article electrical contacts 52. Each electrical fuse 54 is positioned proximate a portion of the aerosol-forming substrate 42 that is heated by one of the electrical heaters 24 of the aerosol-generating device 12 during use. The article electrical contacts 52 and the electrical fuses 54 are connected in series so that they form a continuous ring around a portion of the cylindrical outer surface of the aerosol-generating article 12.

The article electrical contacts 52 and the device electrical contacts 25 are configured so that, when the aerosol-generating article 40 is received within the cavity 17 of the aerosol-generating device 12, each article electrical contact 52 contacts a single device electrical contact 25, regardless of the rotational orientation of the aerosol-generating article 40 within the cavity 17. During use, the controller 22 supplies electrical energy from the supply of electrical energy 18 to consecutive pairs of device electric contacts 25. By supplying electrical energy to consecutive pairs of device electrical contacts 25, the controller 22 can measure the electrical resistance of each electrical fuse 54 via the device electrical contacts 25 and the corresponding pair of article electrical contacts 52. Based on the measured electrical resistances, the controller 22 sequentially controls a supply of electrical current from the supply of electrical energy 18 to each of the electrical heaters 24 to heat a corresponding portion of the aerosol-forming substrate 42 of the aerosol-generating article 40, which releases volatile compounds from the tobacco for delivery to the user.

Figure 3:
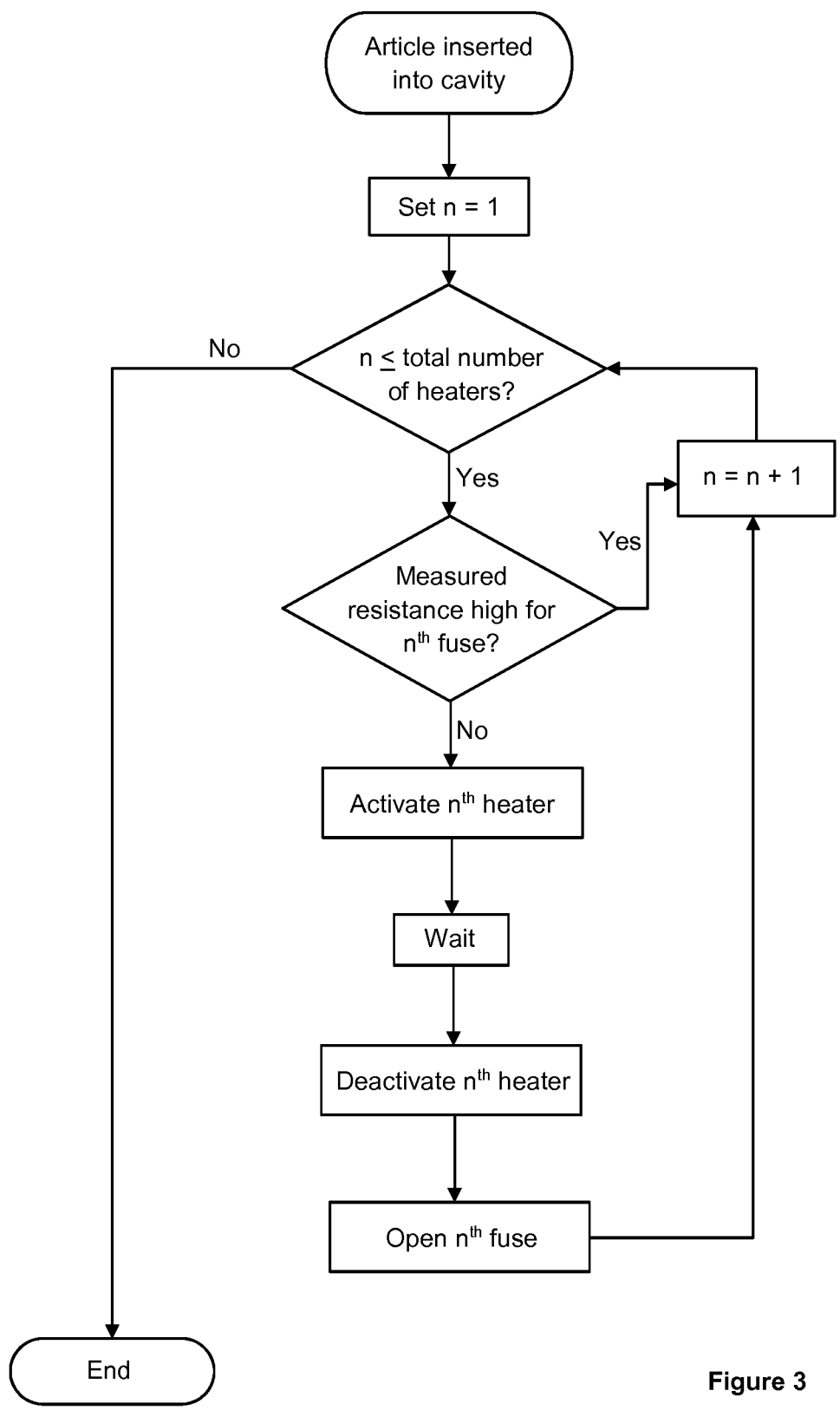
FIG. 3 shows a flow diagram illustrating the steps performed by the controller of the aerosol-generating device of FIG. 1 during heating of the aerosol-generating article.

FIG. 3 shows a flow diagram illustrating the main process steps performed by the controller 22 during sequential heating of the aerosol-forming substrate 42. When the aerosol-generating article 40 is inserted into the cavity 17 and the aerosol-generating device 12 is activated, the controller 22 sets a counter, n, to a value of 1. Next, the controller 22 determines whether the current value of n is less than or equal to the total number of electrical heaters 24. If the answer is no, the controller 22 determines that all portions of the aerosol-forming substrate 42 have been heated and the process of activating the electrical heaters 24 is terminated for the current aerosol-generating article 40. If the answer is yes, the controller 22 supplies electrical energy to the $n^{th}$ pair of device electrical contacts 25 to measure the electrical resistance of the $n^{th}$ electrical fuse 54.

If the measured electrical resistance is higher than a threshold value, the controller 22 determines that the $n^{th}$ electrical fuse has been opened and that the corresponding portion of the aerosol-forming substrate 42 has been heated previously, for example during a previous partial use of the aerosol-generating article 40. In this case, the corresponding $n^{th}$ electrical heater 24 is not activated, the controller 22 increases the value of n by 1 and the process repeats from the step of determining whether the current value of n is less than or equal to the total number of electrical heaters 24.

If the measured electrical resistance is lower than a threshold value, the controller 22 determines that the $n^{th}$ electrical fuse is closed and that the corresponding portion of the aerosol-forming substrate 42 has not been heated. In this case, the controller 22 activates the corresponding $n^{th}$ electrical heater 24 for a predetermined period of time. After the predetermined period of time has elapsed, the controller 22 deactivates the $n^{th}$ electrical heater 24 and supplies sufficient electrical energy to the $n^{th}$ electrical fuse to open the $n^{th}$ electrical fuse. The controller 22 then increases the value of n by 1 and the process repeats from the step of determining whether the current value of n is less than or equal to the total number of electrical heaters 24.

The skilled person will appreciate that the step of opening the n$^{th}$ electrical fuse can be effected at any time between the controller 22 determining that the measured electrical resistance is lower than the threshold value and the step of increasing the value of n by 1.

At the end of the process illustrated in FIG. 3, the controller 22 supplies electrical current from the supply of electrical energy 18 to the feedback device 20 to provide feedback to the user to indicate the end of the heating process.

Figure 4:
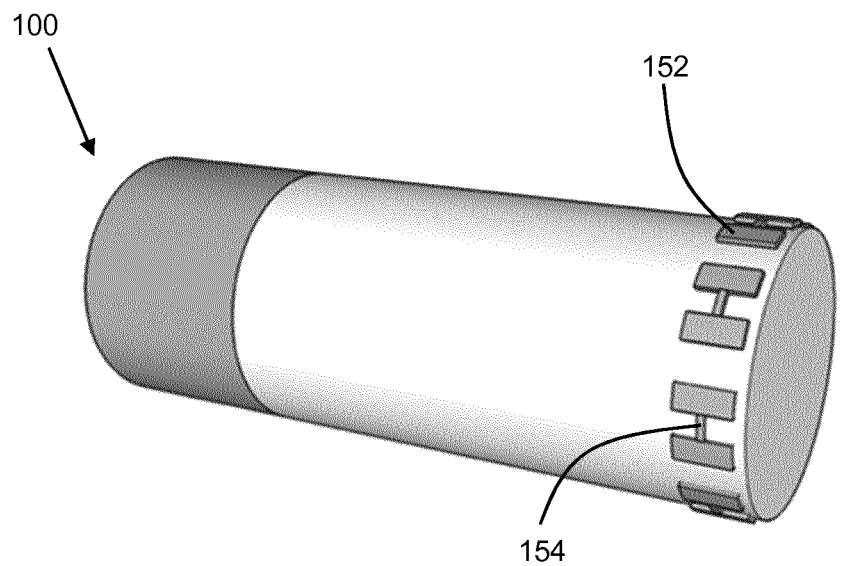
FIG. 4 shows an aerosol-generating article according to a second embodiment of the present invention.

FIG. 4 shows an alternative arrangement of the article electrical contacts on an aerosol-generating article 100 according to a second embodiment of the present invention. The aerosol-generating article 100 comprises a plurality of article electrical contacts 152 and a plurality of electrical fuses 154, wherein each article electrical contact 152 is connected only to a single electrical fuse 154. Therefore, pairs of article electrical contacts 152 each with an electrical fuse 154 extending between them form discrete fuse units on the aerosol-generating article 100. As such, the aerosol-generating article 100 shown in FIG. 4 may comprise fewer electrical fuses than the aerosol-generating article 40 shown in FIG. 2 and may be suited to an aerosol-generating device comprising fewer electrical heaters. Otherwise, the use of the aerosol-generating article 100 in an aerosol-generating system is substantially the same as the use of the aerosol-generating article 40, as described with reference to FIGS. 1 to 3.

Figure 5:
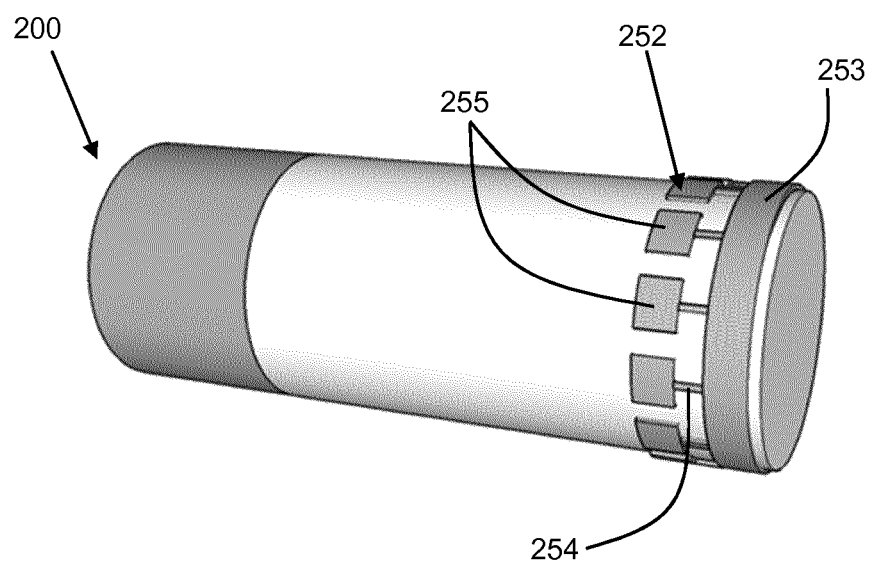
FIG. 5 shows an aerosol-generating article according to a third embodiment of the present invention.

FIG. 5 shows a further alternative arrangement of the article electrical contacts on an aerosol-generating article 200 according to a third embodiment of the present invention. The aerosol-generating article 200 comprises a plurality of article electrical contacts 252 comprising a common article electrical contact 253 and a plurality of sensing article electrical contacts 255. The aerosol-generating article 200 further comprises a plurality of electrical fuses 254, each electrical fuse 254 extending between and electrically connected to the common article electrical contact 253 and a sensing article electrical contact 255. For use with the aerosol-generating article 200, an aerosol-generating device comprises a common device electrical contact for contacting the common article electrical contact 253 and a plurality of sensing device electrical contacts each for contacting a sensing article electrical contact 255. In use, the controller of the aerosol-generating device measures the electrical resistance between the common article electrical contact 253 and each of the sensing article electrical contacts 255 to determine whether the corresponding electrical fuse 254 is closed or open. Otherwise, the operation of an aerosol-generating system comprising the aerosol-generating article 200 is substantially the same as the operation of the aerosol-generating system 10 described with reference to FIGS. 1 to 3.

Figure 6:
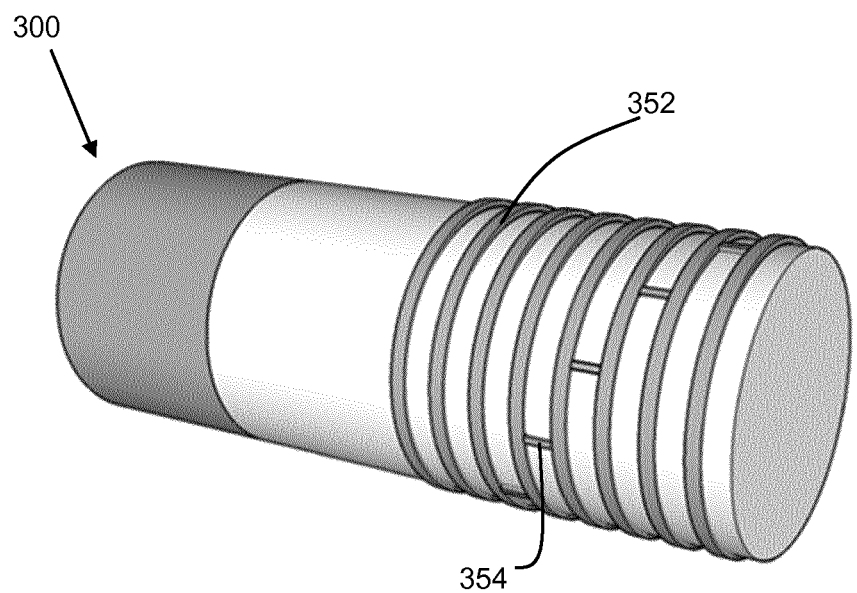
FIG. 6 shows an aerosol-generating article according to a fourth embodiment of the present invention.

FIG. 6 shows a further alternative arrangement of the article electrical contacts on an aerosol-generating article 300 according to a fourth embodiment of the present invention. The aerosol-generating article 300 comprises a plurality of annular article electrical contacts 352 spaced apart along a portion of the length of the aerosol-generating article 300. The aerosol-generating article further comprises a plurality of electrical fuses 354, wherein each electrical fuse 354 extends between and is electrically connected to a pair of the article electrical contacts 352. For use with the aerosol-generating article 300, an aerosol-generating device comprises a plurality of device electrical contacts spaced apart along part of a length of a cavity for receiving the aerosol-generating article 100. Otherwise, the operation of an aerosol-generating system comprising the aerosol-generating article 300 is substantially the same as the operation of the aerosol-generating system 10 described with reference to FIGS. 1 to 3.

Figure 7:
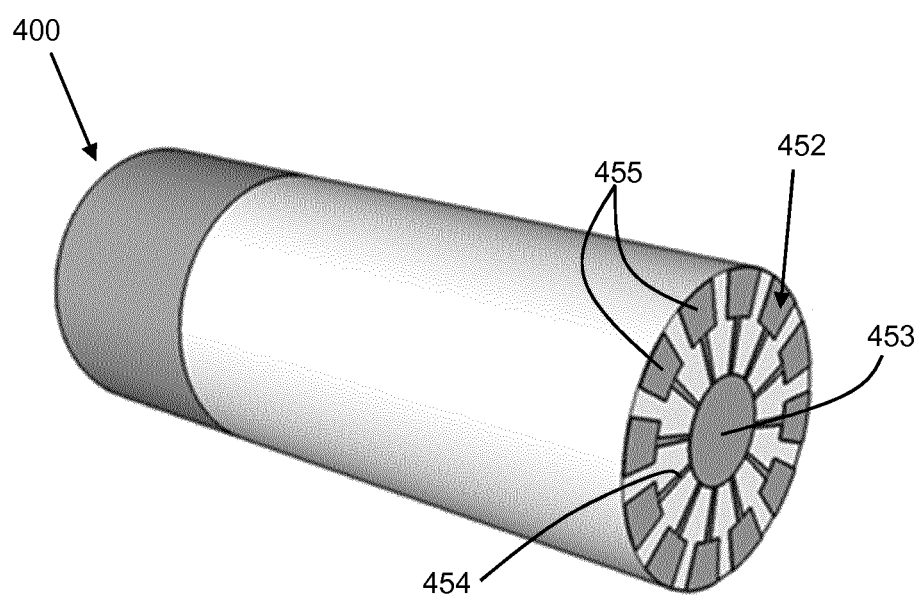
FIG. 7 shows an aerosol-generating article according to a fifth embodiment of the present invention.

FIG. 7 shows a further alternative arrangement of the article electrical contacts on an aerosol-generating article 400 according to a fifth embodiment of the present invention. The aerosol-generating article 400 comprises a plurality of article electrical contacts 452 positioned on an end face of the aerosol-generating article 400. The plurality of article electrical contacts 452 comprises a common article electrical contact 453 positioned at the centre of the end face and a plurality of sensing article electrical contacts 455 positioned around the common article electrical contact 453. The aerosol-generating article 400 further comprises a plurality of electrical fuses 454, each electrical fuse 454 extending between and electrically connected to the common article electrical contact 453 and a sensing article electrical contact 455. For use with the aerosol-generating article 400, an aerosol-generating device comprises a common device electrical contact for contacting the common article electrical contact 453 and a plurality of sensing device electrical contacts each for contacting a sensing article electrical contact 455, the device electrical contacts positioned on an end face of a cavity for receiving the aerosol-generating article 400. In use, the controller of the aerosol-generating device measures the electrical resistance between the common article electrical contact 453 and each of the sensing article electrical contacts 455 to determine whether the corresponding electrical fuse 454 is closed or open. Otherwise, the operation of an aerosol-generating system comprising the aerosol-generating article 400 is substantially the same as the operation of the aerosol-generating system 10 described with reference to FIGS. 1 to 3.

The invention claimed is:
1. An aerosol-generating article, comprising:
an aerosol-forming substrate;
a plurality of electrical fuses spaced apart from each other, each electrical fuse of the plurality of electrical fuses disposed proximate a portion of the aerosol-forming substrate; and
at least three article electrical contacts,
wherein said each electrical fuse extends between and is electrically connected to a pair of the article electrical contacts, and
wherein the at least three article electrical contacts and the plurality of electrical fuses each extend over a portion of an outer surface of the aerosol-forming substrate.

2. The aerosol-generating article according to claim 1, wherein the aerosol-forming substrate has a substantially cylindrical outer surface.

3. The aerosol-generating article according to claim 2, wherein the at least three article electrical contacts and the plurality of electrical fuses are connected in series so that each article electrical contact of the at least three article electrical contacts is electrically connected to at least two electrical fuses of the plurality of electrical fuses, and so that the at least three article electrical contacts and the plurality of electrical fuses form a continuous ring around the portion of the cylindrical outer surface.

4. The aerosol-generating article according to claim 2, wherein each article electrical contact of the at least three article electrical contacts is connected to only a single electrical fuse of the plurality of electrical fuses.

5. The aerosol-generating article according to claim 2, wherein each article electrical contact of the at least three article electrical contacts has a substantially annular shape, and
wherein the at least three article electrical contacts are spaced apart along at least the portion of the cylindrical outer surface.

6. The aerosol-generating article according to claim 1, wherein the at least three article electrical contacts comprise a common article electrical contact and a plurality of sensing article electrical contacts, and
wherein said each electrical fuse extends between a sensing article electrical contact of the plurality of sensing article electrical contacts and the common article electrical contact.

7. The aerosol-generating article according to claim 6, wherein the aerosol-forming substrate has a substantially cylindrical outer surface, and
wherein the common article electrical contact has a substantially annular shape and extends around a portion of the substantially cylindrical outer surface.

8. The aerosol-generating article according to claim 6, wherein the aerosol-forming substrate is substantially elongate and comprises an end face, and
wherein the at least three article electrical contacts are disposed on the end face.

9. The aerosol-generating article according to claim 8, wherein the common article electrical contact is disposed at the center of the end face, and
wherein the plurality of sensing article electrical contacts are spaced around the common article electrical contact.

10. An aerosol-generating device, comprising:
a housing defining a cavity configured to receive an aerosol-generating article;
a supply of electrical energy;
a plurality of electrical heaters disposed within the cavity;
at least three device electrical contacts disposed within the cavity and configured to electrically connect to a plurality of electrical fuses on an aerosol-generating article when the aerosol-generating article is received within the cavity, wherein each electrical heater of the plurality of electrical heaters is associated with a pair of the device electrical contacts; and
a controller configured to measure electrical resistance between the pair of the device electrical contacts when the aerosol-generating article is received within the cavity, and to control the supply of the electrical energy to each electrical heater of the plurality of electrical heaters based on a measured electrical resistance between a corresponding pair of the device electrical contacts.

11. The aerosol-generating device according to claim 10, wherein the at least three device electrical contacts comprise a common device electrical contact and a plurality of sensing device electrical contacts, and
wherein the controller is further configured to measure the electrical resistance between each sensing device electrical contact of the plurality of sensing device electrical contacts and the common device electrical contact when the aerosol-generating device is received within the cavity.

12. An aerosol-generating system, comprising:
an aerosol-generating article comprising:
an aerosol-forming substrate, and
a plurality of electrical fuses spaced apart from each other, each electrical fuse of the plurality of electrical fuses disposed proximate a portion of the aerosol-forming substrate; and
an aerosol-generating device according to claim 10.

13. An aerosol-generating system, comprising:
an aerosol-generating article comprising an aerosol-forming substrate and a plurality of electrical fuses spaced apart from each other, each electrical fuse of the plurality of electrical fuses disposed proximate a portion of the aerosol-forming substrate; and
an aerosol-generating device comprising:
a housing defining a cavity configured to receive the aerosol-generating article,
a supply of electrical energy,
a plurality of electrical heaters disposed within the cavity,
at least three device electrical contacts disposed within the cavity, wherein each electrical heater of the plurality of electrical heaters is associated with a pair of the device electrical contacts, and wherein the pair of the device electrical contacts is configured to electrically connect to an electrical fuse of the plurality of electrical fuses when the aerosol-generating article is received within the cavity, and
a controller configured to perform the following steps for each electrical heater of the plurality of electrical heaters when the aerosol-generating article is received within the cavity:
measure an electrical resistance between a corresponding pair of device electrical contacts among the least three device electrical contacts,
when the measured electrical resistance is indicative of a closed electrical fuse on the aerosol-generating article, control a first supply of the electrical energy to said each electrical heater to heat the portion of the aerosol-forming substrate proximate a closed electrical fuse of the plurality of electrical fuses, and
control a second supply of the electrical energy to the corresponding pair of device electrical contacts among the least three device electrical contacts to open the closed electrical fuse.

14. A controller for an aerosol-generating device having a power supply and a plurality of electrical heaters, the controller being configured to perform the following steps when an aerosol-generating article having an aerosol-forming substrate and a plurality of electrical fuses is received within the aerosol-generating device:
measure an electrical resistance of one or more electrical fuses of the plurality of electrical fuses on the aerosol-generating article;
select an electrical heater among the plurality of electrical heaters associated with a closed electrical fuse among the plurality of electrical fuses based on the measured electrical resistance;
trigger a first supply of the electrical energy from the power supply to the selected electrical heater to heat a portion of the aerosol-forming substrate; and
trigger a second supply of the electrical energy from the power supply to the closed electrical fuse to open the closed electrical fuse.

* * * * *